US00PP15826P2

(12) United States Plant Patent
Jensen

(10) Patent No.: US PP15,826 P2
(45) Date of Patent: Jul. 5, 2005

(54) ***CAMPANULA* PLANT NAMED 'PKMP03'**

(50) Latin Name: *Campanula portenschlagiana Schult.*
Varietal Denomination: PKMp03

(75) Inventor: Gert Kim Jensen, Odense N (DK)

(73) Assignee: Gartneriet Pkm Aps, Odense N (DK)

( * ) Notice: Subject to any disclaimer, the term of this patent is extended or adjusted under 35 U.S.C. 154(b) by 19 days.

(21) Appl. No.: 10/788,300

(22) Filed: Mar. 1, 2004

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—June Hwu
(74) *Attorney, Agent, or Firm*—Foley & Lardner LLP

(57) ABSTRACT

A distinct cultivar of *Campanula* plant named 'PKMp03', characterized by its compact plant habit; dense and bushy plant form; vigorous growth habit; large upright to outward facing, white, single bell flowers, high number of flowers per plant, no need for vernalization.

4 Drawing Sheets

Genus and species of the plant claimed: *Campanula portenschlagiana Schult.*
Variety denomination: 'PKMp03'.

BACKGROUND OF THE INVENTION

The present Invention relates to a new and distinct cultivar of *Campanula* plant, botanically known as *Campanula portenschlagiana Schult.,* commonly known as Dalmatian Bellflower, and hereinafter referred to by the name 'PKMp03'.

The new *Campanula* is a product of a planned breeding program conducted by the Inventor, Gert K. Jensen, in Søhus, Denmark. The new *Campanula* originated from a cross made in 2003 by the Inventor between a proprietary selection of *Campanula portenschlagiana Schult.* named '08.02.03' (unpatented) as the female parent and a proprietary selection of *Campanula portenschlagiana Schult.* named '08.02.04' (unpatented) as the male parent. The Inventor selected the new *Campanula* cultivar from the progeny of the above crossing in 2003 on the basis of its white flowers.

The new *Campanula* cultivar was first asexually reproduced in June, 2003, by terminal vegetative cuttings on stock plants in Søhus, Denmark. Horticultural examination of plants grown from cuttings of the plant in Søhus, Denmark, and continuing thereafter, has demonstrated that the combination of characteristics as herein disclosed for 'PKMp03' are firmly fixed and are retained through successive generations of asexual reproduction. The new cultivar reproduces true to type.

BRIEF SUMMARY OF THE INVENTION

Plants of the cultivar 'PKMp03' have not been observed under all possible environmental conditions. The phenotype may vary somewhat with variations in environment such as temperature, light intensity, day length, and fertility level without, however, any variance in genotype.

The following traits have been repeatedly observed and are determined to be the unique characteristics of 'PKMp03'. These characteristics in combination distinguish 'PKMp03' as a new and distinct cultivar.

1. Large upright to outward facing, white, single bell flowers.
2. High number of flowers per plant.
3. Dense and bushy plant form, mainly due to higher number of laterals.
4. Spreading but compact and regular plant habit.
5. No need for vernalization.

Plants of the cultivar 'PKMp03' can be compared to the parental cultivars *Campanula portenschlagiana Schult.* '08.02.03' and '08.02.04'. The new cultivar 'PKMp03' differs from the parental cultivar in the following ways:

Flowers of the new *Campanula* are white whereas flowers of the parental cultivars are blue. Plants of the new *Campanula* have less upright growth habit than plants of the parental cultivars. Plants of the new *Campanula* have yellow-green leaves whereas the leaves of the parental cultivars are green. Plants of the new *Campanula* have more flowers per plant than the plants of the parental cultivars. Plants of the new *Campanula* have differently shaped corolla lobes than the plants of the parental cultivars.

BRIEF DESCRIPTION OF THE PHOTOGRAPHS

The accompanying color photographs illustrate the overall appearance of the new cultivar, showing the colors as true as it is reasonably possible to obtain in color reproductions of this type. Colors in the photographs may differ slightly from the color values cited in the detailed botanical description, which more accurately describe the actual colors of the new *Campanula.*

The first photograph shows a top view of a full flowering plant of 'PKMp03' as grown in an 11 cm pot.

The second photograph shows a side view of a full flowering plant of 'PKMp03' as grown in an 11 cm pot.

The third photograph shows the flowers and leaves of 'PKMp03' compared to the female parent '08.02.03' (to the right) and the male parent '08.02.04' (to the left).

The fourth photograph shows a close-up view of typical single flowers of 'PKMp03'.

DETAILED BOTANICAL DESCRIPTION

In the following description, color references are made to The Royal Horticultural Society Colour Chart, $4^{th}$ edition, where general terms of ordinary dictionary significance are used. Plants were grown under greenhouse conditions as stated in the detailed description sheet. Plants used for this description were grown for about 14 weeks after cutting in 11 cm pots. The new cultivar plant examined has not been treated with growth retardant.

Botanical classification: *Campanula portenschlagiana Schult.* cultivar 'PKMp03'.

Parentage:

*Female parent.*—Proprietary selection of *Campanula portenschlagiana Schult.* named '08.02.03' (unpatented).

*Male parent.*—*Campanula portenschlagiana Schult.*, named '08.02.04' (unpatented).

Propagation: By terminal vegetative cuttings produced on stock plants kept warm and in short days.

Time to initiate roots: About 10 to 14 days at 18 to 21 C in tunnels in a greenhouse.

Root description: Fine, well branched.

Plant description:

Form: Perennial plant with ascending to spreading plant habit. *Campanulate* flowers in racemes. Freely branching with secondary lateral branches forming at every node; dense and bushy. Freely branching, somewhat brittle stems. Plant spread=25–30 cm.

Crop time: After rooting, about 14 weeks are required to produce finished flowering plants in 11 cm pots.

Plant height (soil level to top of plant plane): About 10 cm.

Vigor: Vigorous growth rate.

Lateral branch description:

*Length.*—11–13 cm.

*Texture.*—Soft.

*Color.*—144B, yellow-green.

Petiole description:

*Length.*—Basal 4–6 cm, Apical 0–15 mm.

*Diameter.*—0.5–1 mm.

*Texture.*—Soft, flexible.

*Color.*—138C, green.

Foliage description: Leaves alternate, single, dentate, palmate (actinodromus), not very conspicuous venation.

*Basal leaf length.*—15–20 mm.

*Width.*—About 25 mm.

*Shape.*—Cordate.

*Apex.*—Rounded.

*Base.*—Cordate.

*Margin.*—Broadly dentate.

*Texture.*—Smooth, glabrous, dull. Short stiff hairs on abaxial side and along veins and margin.

*Color.*—Young foliage, upper and lower surfaces: 146A and 146C, yellow-green. Mature foliage, upper and lower surfaces: 137A and 137B. Venation, 137D.

Flower description:

Flower arrangement and shape: Many single flowers in racemes; white *Campanulate* flowers with small star shaped calyx.

Natural flowering season: Continuous throughout the spring and summer. Season can be extended by long day treatments.

Flower longevity on the plant: 10–14 days. Longevity of individual flowers is highly dependent on temperature and light conditions. Flowers persistent.

Flower fragrance: None.

Inflorescence size:

*Length.*—About 11 cm.

*Diameter.*—4–6 cm.

Flower buds: 155D whiter, a slight tinge of 85D (tinge of 85D disappears upon anthesis) on upper parts of opening corolla, buds up to 14 mm long and 5 mm wide before anthesis.

Flowers:

*Upright, length.*—About 17 mm.

*Diameter.*—About 25 mm.

Petals:

*Ovate, acuminate petal lobes.*—10 mm long and 6 mm wide.

*Number.*—5.

*Margin.*—Entire.

*Texture.*—Velvety.

*Corolla color.*—Upper and lower surfaces, whiter than 155D.

Sepals:

*Number.*—5.

*Size.*—Length 6 mm, width 1 mm.

*Shape.*—Linear.

*Apex (tip) shape.*—Cuspidate.

*Margin.*—Whole.

*Color.*—143A, green.

Pistil and stigma: Conspicuous tripartite, white RHS 155D.

*Pistal number.*—1.

*Style.*—Length: 11 mm.

*Ovary.*—Color: 150D, yellow-green.

Stamen number: 5.

*Anther.*—Size: 1 mm. Color: 155B, white.

*Pollen.*—Color: 158B, yellow-white.

*Filament.*—Length: 6 mm. Color: 20B, yellow-orange.

Peduncle:

*Strength.*—Moderately pubescent with short stiff hairs.

*Texture.*—Strong.

*Length.*—About 35 mm.

*Diameter.*—About 1 mm.

*Color.*—144B yellow-green.

Seed: Few seeds, 5–10 per flower.

*Length.*—1 mm.

*Diameter.*—0.6 mm.

*Shape.*—Oval. Texture: Smooth and glabrous.

*Color.*—199C, grey-brown.

Fruit: Capsule.

Weather tolerance: Plants of the new *Campanula* have not been tested for tolerance to draught, rain and wind, low temperature, but is expected to be fully hardy in temperate winters (to −20° C.).

Resistant to plant disease: None observed.

Resistance/susceptibility to pest: None observed.

I claim:

1. A new and distinct cultivar of *Campanula* plant named 'PKMp03', as illustrated and described herein.

* * * * *

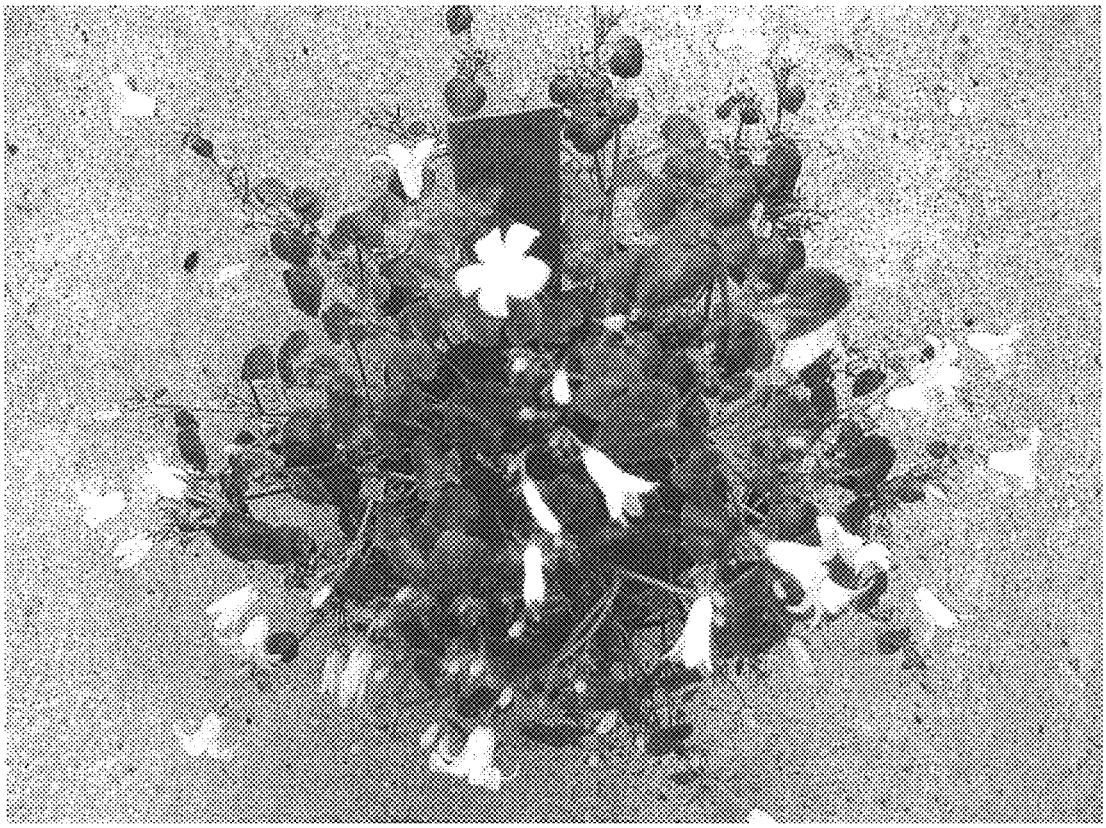

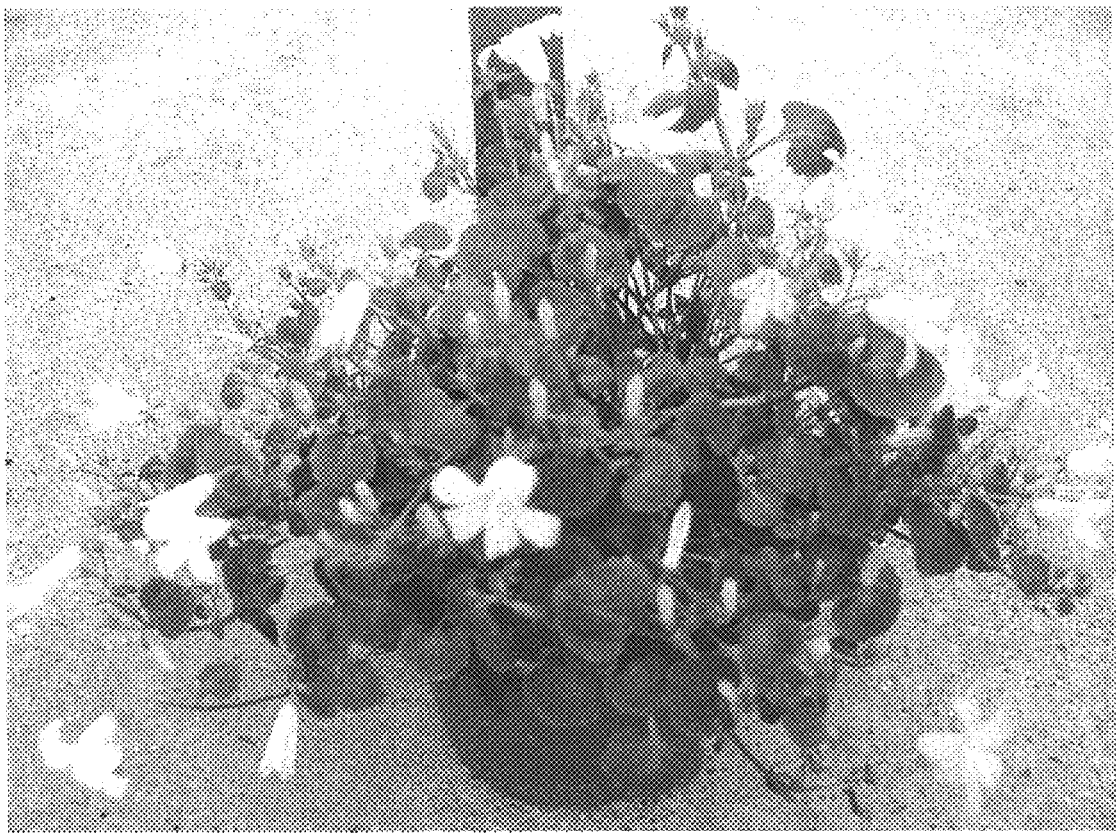

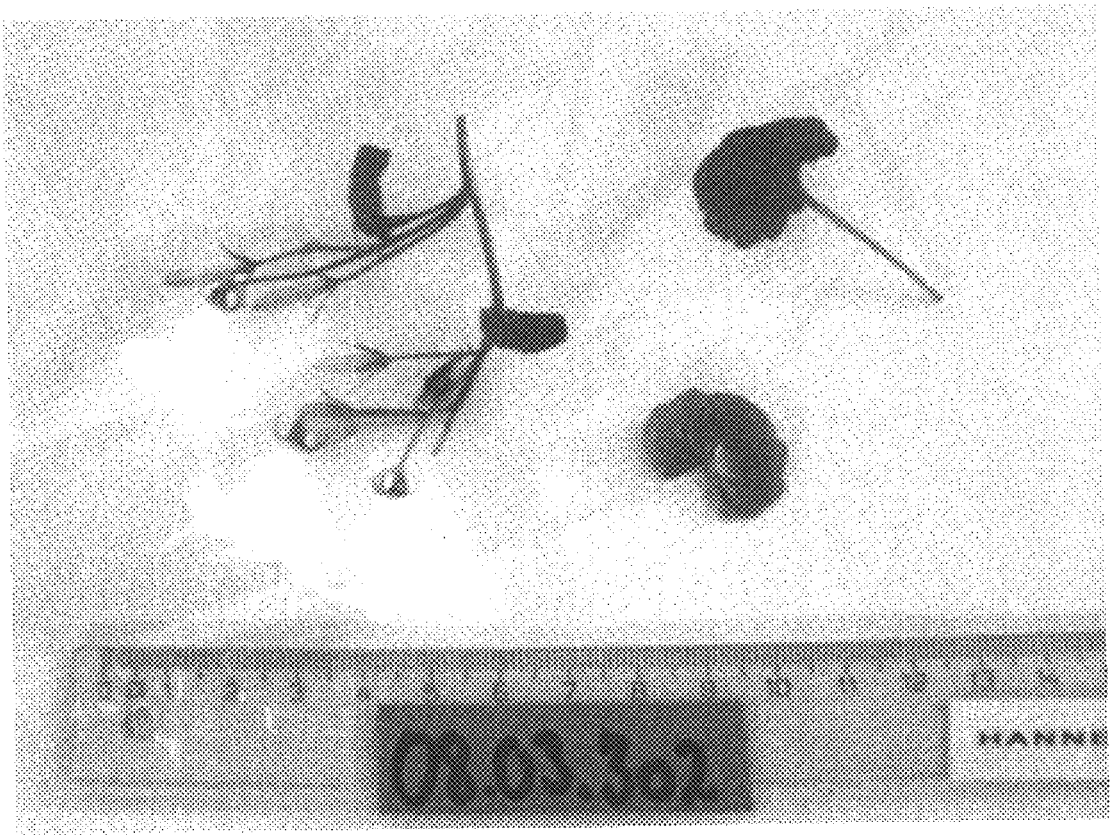

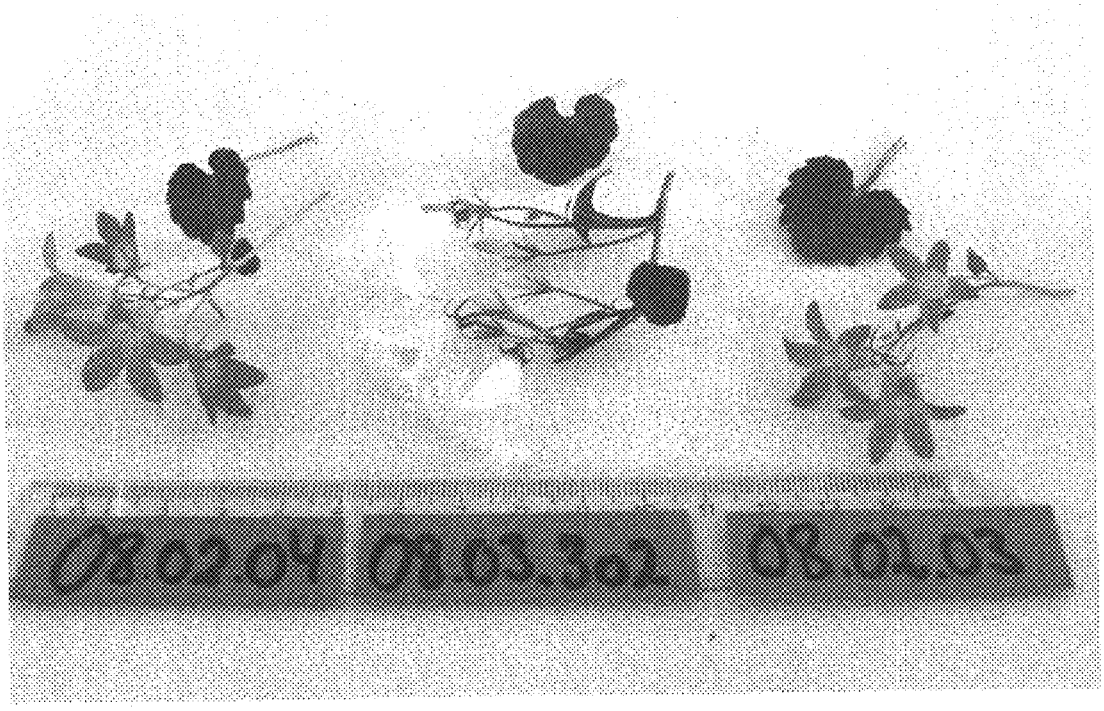
08.02.04
08.03.02
08.02.03